United States Patent [19]

Furutani et al.

[11] 4,272,349
[45] Jun. 9, 1981

[54] CATALYST SUPPORTED OXYGEN SENSOR WITH SENSOR ELEMENT HAVING CATALYST AND PROTECTIVE LAYERS AND A METHOD OF MANUFACTURING SAME

[75] Inventors: Toshinobu Furutani, Toyota; Hiroshi Shinohara, Okazaki; Yasuhiro Otsuka, Toyota; Shinichi Matsumoto, Toyota; Hiroshi Wakisaka, Toyota, all of Japan

[73] Assignee: Toyota Jidosha Kogyo Kabushiki Kaisha, Toyota, Japan

[21] Appl. No.: 115,450

[22] Filed: Jan. 25, 1980

[30] Foreign Application Priority Data

Feb. 7, 1979 [JP] Japan .................................. 54-13098
Feb. 7, 1979 [JP] Japan .................................. 54-13099

[51] Int. Cl.³ .............................................. G01N 27/46
[52] U.S. Cl. .................................. 204/195 S; 204/1 T
[58] Field of Search ............................ 204/1.5, 195 S

[56] References Cited

U.S. PATENT DOCUMENTS

| | | | |
|---|---|---|---|
| 3,928,161 | 12/1975 | McIntyre et al. | 204/195 S |
| 3,935,089 | 1/1976 | Togawa et al. | 204/195 S |
| 3,978,006 | 8/1976 | Topp et al. | 204/195 S |
| 4,021,326 | 5/1977 | Pollner et al. | 204/195 S |
| 4,040,930 | 8/1977 | Dillon | 204/195 S |
| 4,116,795 | 9/1978 | DeJong | 204/195 S |
| 4,116,797 | 9/1978 | Akatsuka | 204/195 S |
| 4,119,512 | 10/1978 | Inoue et al. | 204/195 S |
| 4,132,615 | 1/1979 | Linder et al. | 204/195 S |

FOREIGN PATENT DOCUMENTS

| | | | |
|---|---|---|---|
| 2656648 | 6/1977 | Fed. Rep. of Germany | 204/195 S |
| 2748461 | 5/1978 | Fed. Rep. of Germany | 204/195 S |

Primary Examiner—T. Tung
Attorney, Agent, or Firm—Stevens, Davis, Miller & Mosher

[57] ABSTRACT

An oxygen sensor with an oxygen sensor element having an outer protective layer of alumina, acting as getters with respect to catalyst poisons, particularly phosphorus, in exhaust gases, formed on the outer surface of a catalyst layer of platinum or a mixture of platinum and rhodium which is coated on an electrode protective layer provided on the outer electrode of an oxygen sensor element. Such an outer protective layer is additionally provided on the inner wall of the inner louver of the oxygen sensor having a double louver structure. A method of manufacturing an oxygen sensor with an oxygen sensor element comprising the steps of coating such an outer alumina protective layer onto the outer surface of said catalyst layer formed on an electrode protective layer provided onto the outer electrode of an oxygen sensor element and additionally coating such an alumina protective layer onto the inner wall of the inner louver of an oxygen sensor having a double louver structure.

10 Claims, 6 Drawing Figures

CATALYST SUPPORTED OXYGEN SENSOR WITH SENSOR ELEMENT HAVING CATALYST AND PROTECTIVE LAYERS AND A METHOD OF MANUFACTURING SAME

BACKGROUND OF THE INVENTION

1. Field of the Invention

The present invention relates to an improvement of a catalyst supported oxygen sensor with a sensor element having a catalyst layer and a catalyst protective layer and a method of manufacturing the same and, more particularly, to such an oxygen sensor having additionally an inner layer and a protective layer on the inner louver of the sensor and a method of the manufacture of the same. The protective layers on the sensor element and additionally on the inner louver can act as getters with respect to catalyst poisons caused by phosphorus in exhaust gases from internal combustion engines.

2. Brief Description of the Prior Art

In a system with respect to the purification of exhaust gases from vehicle internal combustion engines, it is of significance to determine oxygen content in exhaust gases leading to a catalyst converter in order to maintain the composition of exhaust gases within a particular range. In particular, where a so-called three-way system adapted to simultaneously remove non-combusted hydrocarbons, carbon monoxide, and nitrogen oxides is used, the adjustment of the composition of exhaust gases within a very narrow range around the theoretical air-fuel ratio is necessary to provide sufficient purification of the exhaust gases. Oxygen sensors have been used for this purpose to determine oxygen content in exhaust gases and adjust the amount of fuel to be supplied to an internal combustion engine in response to the determination of the oxygen concentration monitored by the oxygen sensor.

Oxygen sensors are provided with an oxygen sensor element generally composed of an oxygen-ion conductive, solid electrolyte which can act as a partition and are so constructed that the electromotive force generated by the difference in the oxygen partial pressures between the reference gas such as air and gases to be measured, such as exhaust gases, is measured to determine the oxygen content in the exhaust gases. When the oxygen sensors of the type conventionally used for this purpose are exposed to exhaust gases from an internal combustion engine in an "unbalanced" state, for example, in which there is excess oxygen in the exhaust gases, that is, an air excess ratio exceeds 1.0 ($\lambda > 1.0$), such oxygen sensors cannot function effectively and they will often give a false signal, for example, a "more air" signal even when there is excess oxygen in the exhaust gases. In order to improve these disadvantages contained in conventional oxygen sensors, it was proposed that a coating layer of oxidizing catalysts was formed on the outer surface of the solid electrolyte body. The oxygen sensors of this type, however, could not provide sufficient catalyst performance during long service when contacted with exhaust gases due to catalyst poisons such as phosphorus, particularly white phosphorus, which are contained therein and will interfere with the catalytic activity of the oxidizing catalyst.

SUMMARY OF THE INVENTION

Accordingly, it is a principal object of the present invention to provide an oxygen sensor with an oxygen sensor element having a catalytically active coating layer which can detract the disadvantages involved in conventional oxygen sensors and sensor elements and can maintain its catalytic activity for a prolonged period of time in service.

It is another object of the present invention to provide an oxygen sensor having an oxygen sensor element with a catalytically active coating layer on the surface of which is provided an outer protective layer serving as protector of a catalyst layer from direct contact with exhaust gases and at the same time as preventer of the catalyst layer from deactivation by catalyst poisons.

It is a further object of the present invention to provide such an oxygen sensor having additionally a catalyst and catalyst protective layers formed on the inner louver of said sensor.

BRIEF DESCRIPTION OF THE DRAWING

FIG. 5 shows the test results obtained by testing a sensor with a sensor element having a catalyst layer and a catalyst protective layer in accordance with the present invention, and FIG. 6 shows the results in which the sensor having a catalyst layer and a catalyst protective layer on the louver thereof was used, together with a sensor element in accordance with the present invention.

DETAILED DESCRIPTION OF THE INVENTION

Figure 1:
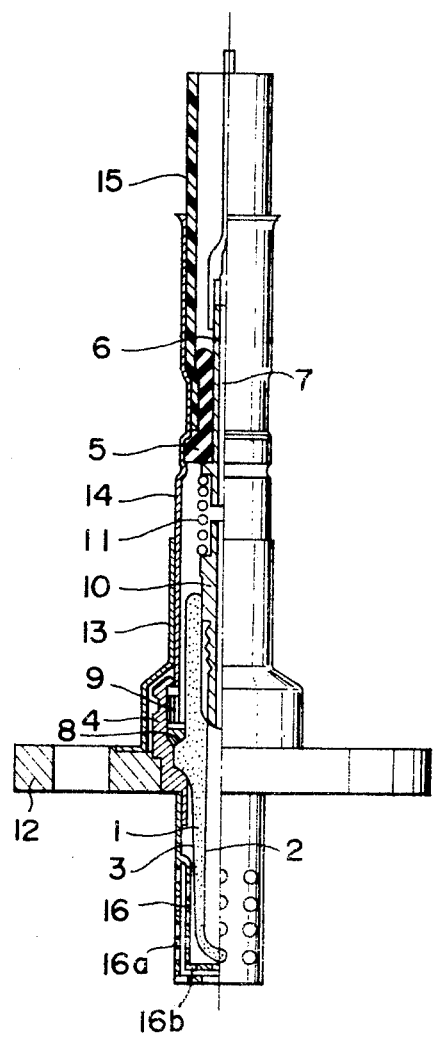
FIG. 1 is a partial, longitudinally sectioned view of an oxygen sensor with an oxygen sensor element positioned therein, in accordance with the present invention.
Figure 2:
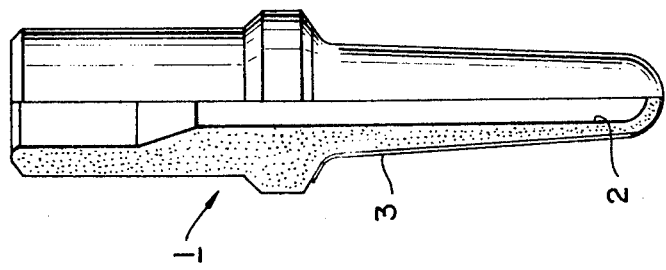
FIG. 2 is a partial, longitudinally sectioned view of an oxygen sensor element in accordance with the present invention.

Referring now to FIGS. 1 and 2, there is shown a hollow, tubular container 1 composed of a solid, oxygen-ion conductive electrolyte with one end portion thereof closed. The electrolyte may be one which has been conventionally used for this purpose and may include zirconia ($ZrO_2$), and $ZrO_2$ containing therein $CaO$, $MgO$, $Y_2O_3$, $Yb_2O_3$, $Sc_2O_3$ or $Nd_2O_3$. On both the inner and outer surfaces of the tubular container is provided a porous layer of, for example, platinum functioning as an inner electrode 2 and an outer electrode 3, respectively, each having a thickness of about 1–3 microns. The inner electrode 2 is constructed so as to bring the atmospheric air as the reference gas into contact with the surface thereof, thereby measuring the oxygen partial pressure of the air inside the tube. The outer electrode 3 is so constructed that the exhaust gases to be measured are brought into contact with the surface thereof through the pores of layers formed on the outer electrode surface. An electrode protective layer 18 (FIG. 3) protecting the outer electrode which is provided on the outer surface of the outer electrode may be formed in a conventional manner, for instance by plasma spraying, on the outer surface of the electrode to provide pores therein through which the exhaust gases to be measured are passed to be brought into contact with the outer electrode.

Figure 3:
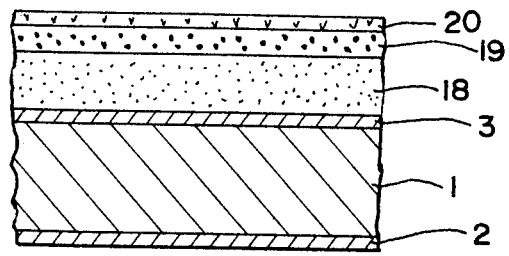
FIG. 3 is an enlarged, partial, schematic representation of a portion of the wall of the oxygen sensor element, represented in the circle "A" in FIG. 2, in accordance with the present invention.

A porous catalyst layer 19 as in FIG. 3 may be composed of catalyst containing, for example, platinum or rhodium or a mixture thereof and coated over the outer surface of the electrode protective layer 18 in a conventional manner, for example, by spraying an aqueous slurry containing the oxid catalyst thereon or dipping the element into such an aqueous slurry, drying at ambient temperature and firing at an appropriate temperature. The resulting catalyst layer 19 is so porous that some components in the exhaust gases passing therethrough may be catalyzed and that the exhaust gases so trated are to pass and reach to the surface of the outer electrode. Platinum may be used singly or in combination with rhodium; however, a mixture of platinum and rhodium in the platinum to rhodium ratio of up to about 7:3 is generally used and the platinum to rhodium ratio of about 9:1 to about 8:2 is preferably used. A greater amount of platinum may decrease the heat resistance of the catalyst layer, while a and a greater amount of rhodium raises the cost of the sensor element. The amount of the catalyst may range from about 1 to about 10 percent by weight and preferably from about 3 to about 5 percent by weight with respect to the weight of the carrier on which the catalyst metal is supported. The carrier may have an average particle size of from about 1 to 10 microns. The thickness of the catalyst layer may be from about 5 to 30 microns and preferably about 12–13 microns. Further, it is preferred to contain about 10 mg. of the catalyst per oxygen sensor element with the outer electrode having the length of about 30 mm. and the total surface are of about 7 cm$^3$. It is to be noted, however, that these parameters will not be restricted to the above described ranges and may be varied depending upon the kind and amount of catalyst metals and carriers or the like.

In accordance with the present invention, an outer protective layer 20 is provided over the surface of the catalyst layer. This protective layer can serve as a coating protecting the catalyst layer from undesirable mechanical influences caused, for example, by direct contact with exhaust gases and at the same time act as a getter with respect to catalyst poisons, in this case, particularly phosphorus present in exhaust gases, thereby preventing the catalyst layer from deactivation and as a result lengthening the life of the catalyst and eventually that of the oxygen sensor element itself. The outer porous protective layer may be coated in conventional manner, for example, by brushing or spraying an aqueous slurry comprising a carrier such as gamma-alumina and a binder such as alumina sol or aluminum nitrate or a mixture thereof on the outer surface of the catalyst layer or dipping a part or the whole of the catalyst layer portion on the sensor element into such an aqueous slurry, drying the wet coating on the element at ambient temperature, and then firing the dried element under conventional conditions. The carrier to be employed for this purpose may be preferably alumina and have an average particle size of preferably from about 5 to 20 microns. The carrier may also be used in an amount of from about 5 to about 20 percent by weight of the binder to be used. The thickness of the protective layer may range from about 5 to about 30 microns and preferably from about 10 to about 20 microns. If the coating thickness of the outer protective layer is too thick, it is undesirable because gas permeability through the pores of the protective layer will be lessened and a response time by an oxygen sensor element is worsened.

Figure 4:
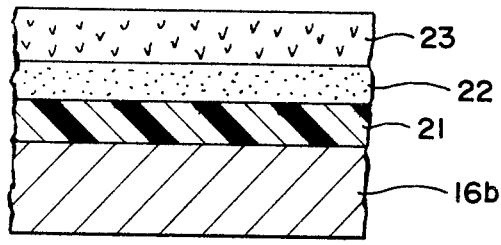
FIG. 4 is an enlarged, partial, schematic representation of a portion of a louver wall of the oxygen sensor in accordance with the present invention.

The oxygen sensor element of the type having a layer structure as described hereinabove may be held and secured in conventional manner in a sensor housing 4 composed of a metal unlikely to be oxidized and transformed at high temperatures of exhaust gases, such as stainless steel. A louver defined below the housing 4 of the sensor is provided in a spaced relation to the sensor element so that the louver covers and protects the sensing portion of the sensor element. The closed lower portion of the louver is so constructed to be of a double-wall structure which comprises an outer wall referred to as an outer louver 16a and an inner wall referred to as an inner louver 16b and the upper portion thereof to be of a single wall structure. The single wall portion of the louver extends to the middle portion thereof and then separates into two walls referred to as the outer and inner louvers 16a, 16b in which the inner louver 16b extends inwardly, downwardly in an equally spaced relation to the outer louver 16a and in parallel thereto. The two louvers each have a number of openings through which exhaust gases can be passed and brought into contact with the oxygen sensor element positioned in an oxygen sensor housing. The louver is made of a material identical with or similar to that of the housing of the sensor. As in FIG. 4, the inner louver 16b is provided with a three layer coating. The utmost inner layer 21 formed in direct contact with the louver 16b is composed of, for example, a Ni-Cr-Al layer which can act as a buffer to lessen a heat expansion of the louver material. The layer 21 is formed on the surface of the inner louver 16b which is previously roughened, for example, by sand blast techniques and then heated at 800°–1,000° C. in a diffusion furnace. A layer 22 is then carried onto the surface of the layer 21 in conventional manner, for example, by plasma flame spraying alumina such as α-alumina or MgOAl$_2$O$_3$ spinel in a proper amount in substantially the same manner as with the coating carried out in forming the catalyst layer on the sensor element. A protective layer 23 is additionally formed on the outer surface of the inner layer with substantially the same composition in substantially the same manner and having the same thickness as the protective layer formed on the catalyst layer 19 of the sensor element, as described above. The protective layer 23 formed, like the outer protective layer 20, can function as a getter to hold or "trap" phosphorus present in exhaust gases. The effect of providing the protective layer on the louver as in the present invention is that phosphorus causing catalyst poisons passed through the openings of the outer and inner louvers into the inner space defined in the oxygen sensor may be held or trapped in amounts greater than where the sensor having the protective layer in accordance with the present invention is used singly. The phosphorus held or trapped in the protective layers will be converted to aluminum phosphate which does not cause catalyst poisons any longer. When the protective layer formed on the louver decrease its activity for holding or trapping phosphorus present in exhaust gases, a mere replacement of the old louver by a new louver having the same structure and function is sufficient to renew the function, thereby maintaining such sensor performance for a prolonged period of time. The provision of such an outer protective layer on the inner louver also has the advantage of making the coating thickness of the protective layer formed on the sensor element thinner, thereby enhancing the overall sensor performance.

As to the constituent parts of the oxygen sensor according to the present invention other than the oxygen sensor element and the louver, available conventional parts are suitable. As shown in FIG. 1, 5 denotes an insulating plate, 6 a lead wire for taking out an output, 7 a hole for communicating with the atmosphere, 8 graphite, 9 a sealing member of inorganic and metallic materials, 10 a tip for taking out an output, 11 a spring, 12 a flange, 13 a water-proof cover, 14 a cover, and 15 a water-proof tube.

Figure 5:
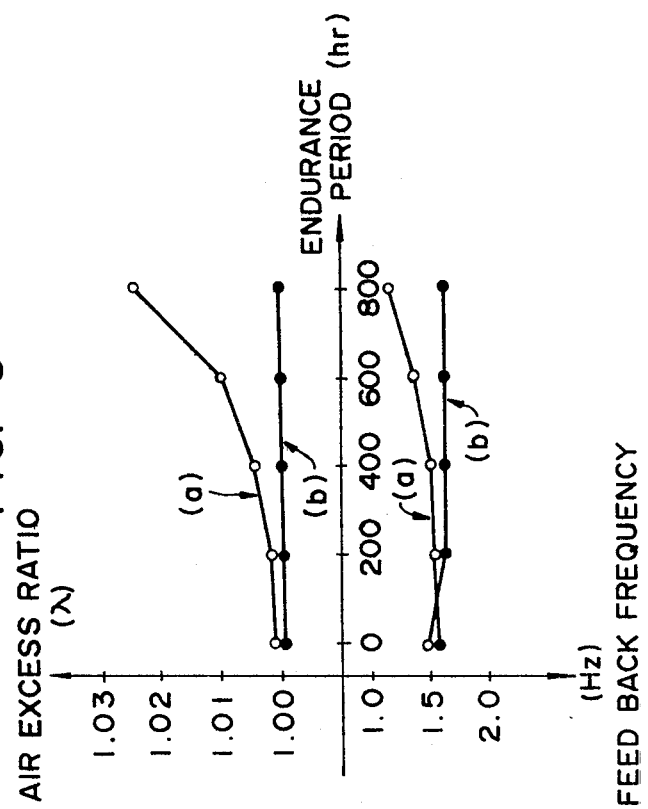
FIGS. 5 and 6 are each a graph illustrating the relationship of an air excess ratio ($\lambda$) and of a feedback frequency (HZ) with an endurance period of the sensor element in accordance with the present invention vs. a conventional oxygen sensor element.
Figure 6:
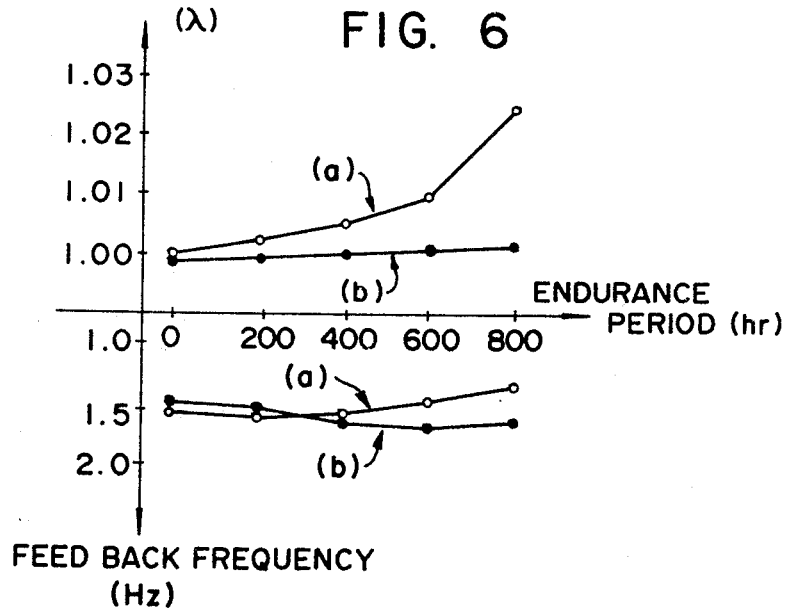

As shown in FIGS. 5 and 6 in which the line referred to as "(a)" means a conventional oxygen sensor element, while the line referred to as "(b)" designates an oxygen sensor element in accordance with the present invention, it is to be noted that the sensor element in accordance with the present invention can maintain an air excess ratio of $\lambda \approx 1$ ($\lambda$ = Actual Air-Fuel Ratio/Theoretical Air-Fuel Ratio) even for 800 hours of duration period, whereas the air excess ratio for the conventional sensor element exceeds one ($\lambda > 1.0$) even after 400 hours of duration period. It is also to be noted that, since the feedback frequency (Hz) for the oxygen sensor element in accordance with the present invention is maintained at substantially the same level even for 800 hours. This means that it can give a constant, correct signal in response to the oxygen content in exhaust gases, whereas the conventional oxygen sensor element cannot operate with accuracy after a 600 hour endurance period.

What I claim is:

1. In an oxygen sensor comprising an oxygen sensor element having an oxygen-ion conductive electrolyte container with one end closed, an inner electrode provided on the inner surface of the electrolyte container, an outer electrode provided on the outer surface thereof, and an electrode protective layer formed on the outer surface of the electrode layer and a louver having an inner and an outer louver positioned over the oxygen sensor element and in a spaced relation to each other, the improvement which comprises a catalyst layer formed on the outer surface of the electrode protective layer, said catalyst layer being protected by an outer catalyst protective layer of alumina, and said inner louver being provided with a three layer coating, the innermost layer acting as a buffer to lessen heat expansion of the louver material, the middle layer being composed of alumina or spinel, and the outer protective layer having substantially the same composition as said catalyst protective layer performing also a function as a catalyst poison getter.

2. An oxygen sensor according to claim 1, wherein said catalyst protective layer is composed of gamma-alumina.

3. An oxygen sensor according to claim 2, wherein said gamma-alumina has an average particle size of from about 5 to about 20 microns.

4. An oxygen sensor according to claim 1, wherein said catalyst protective layer is from about 5 to about 30 microns thick.

5. An oxygen sensor according to claim 4, wherein said catalyst protective layer is from about 10 to 20 microns thick.

6. An oxygen sensor according to claim 1, wherein the outer protective layer is composed of gamma-alumina.

7. An oxygen sensor according to claim 6, wherein the gamma-alumina has an average particle size of from about 5 to about 20 microns.

8. An oxygen sensor according to claim 1, wherein the outer protective layer is from about 5 to about 30 microns thick.

9. An oxygen sensor according to claim 8, wherein the thickness of the outer protective layer is about 10 to 20 microns.

10. A method of manufacturing an oxygen sensor with an oxygen sensor element having an oxygen ion conductive electrolyte container with one end closed, an inner electrode provided on the inner surface of the electrolyte container, an outer electrode provided on the outer surface thereof, and an electrode protective layer formed on the outer surface of the electrode protective layer and a louver having an inner and an outer louver positioned over the oxygen sensor element and in a spaced relation to each other, which comprises forming a catalyst layer on the outer surface of the electrode protective layer, forming an outer catalyst protective layer of alumina on the outer surface of the catalyst layer, forming an innermost buffer layer on said inner louver, forming a middle layer of alumina or spinel on said buffer layer, and forming an outer protective-catalyst poison getter layer having substantially the same composition as said catalyst protective layer on said middle layer.

* * * * *